(12) United States Patent
Koenig et al.

(10) Patent No.: US 7,154,018 B2
(45) Date of Patent: *Dec. 26, 2006

(54) ABSORBENT ARTICLE

(75) Inventors: David W. Koenig, Menasha, WI (US); Lisa M. Kroll, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 423 days.

This patent is subject to a terminal disclaimer.

(21) Appl. No.: 10/028,752

(22) Filed: Dec. 20, 2001

(65) Prior Publication Data

US 2003/0120228 A1    Jun. 26, 2003

(51) Int. Cl.
*A61F 13/15*    (2006.01)
(52) U.S. Cl. ...................... 604/360; 604/359
(58) Field of Classification Search ............... 604/359, 604/360

See application file for complete search history.

(56) References Cited

U.S. PATENT DOCUMENTS

| | | | |
|---|---|---|---|
| 4,100,324 A | 7/1978 | Anderson et al. | |
| 4,167,559 A | 9/1979 | Michel | |
| 4,623,339 A * | 11/1986 | Ciraldo et al. ............... | 604/359 |
| 4,657,766 A | 4/1987 | Goodall | |
| 4,772,479 A | 9/1988 | Goodall | |
| 4,798,603 A | 1/1989 | Meyer et al. | |
| 4,828,860 A | 5/1989 | Goodall | |
| 5,017,562 A | 5/1991 | Holmes et al. | |
| 5,139,779 A | 8/1992 | McNeff | |
| 5,176,668 A | 1/1993 | Bernardin | |
| 5,176,672 A | 1/1993 | Bruemmer et al. | |
| 5,192,606 A | 3/1993 | Proxmire et al. | |
| 5,279,838 A | 1/1994 | McNeff | |
| 5,306,487 A | 4/1994 | Karapasha et al. | |
| 5,364,382 A | 11/1994 | Latimer et al. | |
| 5,482,765 A | 1/1996 | Bradley et al. | |
| 5,486,166 A | 1/1996 | Bishop et al. | |
| 5,490,846 A | 2/1996 | Ellis et al. | |
| 5,507,250 A * | 4/1996 | Reddy et al. ............... | 119/173 |
| 5,509,915 A | 4/1996 | Hanson et al. | |
| 5,518,750 A | 5/1996 | Mcneff | |
| 5,525,346 A | 6/1996 | Hartung et al. | |
| 5,723,149 A | 3/1998 | Bonte et al. | |

(Continued)

FOREIGN PATENT DOCUMENTS

EP    0 565 266 B1    1/1999

(Continued)

OTHER PUBLICATIONS

Wallace, et al., Abstract of "Influence of *Yucca shidigera* Extract on Ruminal Ammonia Concentrations and Ruminal Microorganisms", Appl Environ Microbiol, Jun. 1994, pp. 1762-1767, vol. 60 Issue 6, Rowett Research Institute, Bucksburn, Aberdeen, United Kingdom, PMID 8031077, UI 94304158.

(Continued)

*Primary Examiner*—Tatyana Zalukaeva
*Assistant Examiner*—C. Lynne Anderson
(74) *Attorney, Agent, or Firm*—Senniger Powers (57) ABSTRACT

An absorbent article for absorbing body waste. The includes a permeable liner having a body-facing surface oriented for facing a wearer when the absorbent article is worn and an absorbent-facing surface opposite the body-facing surface, an outer cover, and an absorbent body positioned between the liner and the cover. A *Yucca* sp. extract is positioned between the body-facing surface of the liner and the outer cover.

42 Claims, 2 Drawing Sheets

U.S. PATENT DOCUMENTS

| | | | |
|---|---|---|---|
| 5,730,965 A | | 3/1998 | Rapaport |
| 5,797,891 A | | 8/1998 | Wiersma |
| 5,800,818 A | | 9/1998 | Prugnaud et al. |
| 5,843,056 A | | 12/1998 | Good et al. |
| 5,860,391 A | * | 1/1999 | Maxwell et al. ............ 119/173 |
| 5,879,341 A | | 3/1999 | Odorzynski et al. |
| 5,906,825 A | | 5/1999 | Seabrook, Jr. et al. |
| 5,932,495 A | | 8/1999 | Boney et al. |
| 5,957,906 A | * | 9/1999 | Roe et al. .................... 604/378 |
| 6,029,603 A | * | 2/2000 | Evans et al. ................ 119/171 |
| 6,057,372 A | | 5/2000 | Nobuhiro et al. |
| 6,063,382 A | | 5/2000 | Nakajima et al. |
| 6,159,487 A | | 12/2000 | Znaiden et al. |
| 6,228,265 B1 | * | 5/2001 | Henderson .................. 210/610 |
| 6,309,736 B1 | | 10/2001 | McCormack et al. |
| 6,338,855 B1 | * | 1/2002 | Albacarys et al. .......... 424/409 |
| 6,485,734 B1 | | 11/2002 | Baker et al. |
| 6,552,171 B1 | | 4/2003 | Howard et al. |
| 6,589,892 B1 | * | 7/2003 | Smith et al. ................ 442/414 |
| 6,686,303 B1 | * | 2/2004 | Haynes et al. .............. 442/327 |
| 6,891,079 B1 | * | 5/2005 | Koenig et al. .............. 604/360 |
| 2002/0119173 A1 | | 8/2002 | Lin et al. |
| 2002/0120242 A1 | | 8/2002 | Tyrrell et al. |
| 2002/0136755 A1 | * | 9/2002 | Tyrrell et al. ............... 424/443 |
| 2003/0035785 A1 | * | 2/2003 | Palumbo et al. .......... 424/70.28 |
| 2003/0105445 A1 | * | 6/2003 | Lange et al. ........... 604/385.07 |
| 2003/0118475 A1 | | 6/2003 | Koenig et al. |

FOREIGN PATENT DOCUMENTS

| | | |
|---|---|---|
| EP | 0 776 760 B1 | 5/1999 |
| EP | 0 922 457 A1 | 6/1999 |
| JP | 61 291503 A | 12/1986 |
| JP | 4016163 A2 | 1/1992 |
| JP | 4074105 A2 | 3/1992 |
| JP | 7 107923 | 4/1995 |
| JP | 7149608 A2 | 6/1995 |
| JP | 8019595 A2 | 1/1996 |
| JP | 8119872 A2 | 5/1996 |
| JP | 9187229 A2 | 7/1997 |
| JP | 9328410 A2 | 12/1997 |
| JP | 10045566 A2 | 2/1998 |
| JP | 11147818 | 6/1999 |
| JP | 11200245 A2 | 7/1999 |
| JP | 11322630 A2 | 11/1999 |
| JP | 2000169320 A | 6/2000 |
| JP | 2001 011496 | 1/2001 |
| JP | 2001039812 A | 2/2001 |
| JP | 2002 285472 | 10/2002 |
| KR | 218093 | 10/1999 |
| KR | 2002 090 740 | 12/2002 |
| WO | WO 96/41528 A1 | 12/1996 |
| WO | WO 99/20258 A1 | 4/1999 |
| WO | WO 01/95726 A1 | 12/2001 |
| WO | WO 02/51358 A2 | 7/2002 |

OTHER PUBLICATIONS

Tanako, et al., Abstract of "Application of Saponins in Foods and Cosmetics: Saponins of Mohave Yucca and *Sapindus mukurossi*", Adv Exp Med Biol, 1996, pp. 1-11, vol. 405, Suzugamine Women's College, Hiroshima, Japan, PMID 8910691, UI 97067277 Bibliographical Data only.

Fiers, Sheila A., "Breaking the Cycle: The Etiology of Incontinence Dermatitis and Evaluating and Using Skin Care Products", Ostomy/Wound Management, The Journal for Extended Patient Care Management, Apr. 1996, pp. 32-43, vol. 42, No. 3, USA.

Yeo, et al., Abstract of "Effect of Feeding Diets Containing an Antibiotic, a Probiotic, or Yucca Extract on Growth and Intestinal Urease Activity in Broiler Chicks", Poult Sci, Feb. 1997, pp. 381-385, vol. 76, Issue 2, Department of Animal Science, Cheju National University, Republic of Korea, PMID 9057222, UI 97210047.

Lowe, et al., Abstract of "The Ameliorating Effect of *Yucca schidigera* Extract on Canine and Feline Faecal Aroma", Res Vet Sci, Jul.-Aug. 1997, pp. 61-66, vol. 63, Issue 1, Gilbertson and Page Ltd., Welwyn Garden City, USA, PMID 9368958, UI 98035433.

Lowe, et al., Abstract of "The Effect of *Yucca schidigera* Extract on Canine and Feline Faecal Volatiles Occurring Concurrently with Faecal Aroma Amelioration", Res Vet Sci, Jul.-Aug. 1997, pp. 67-71, vol. 63, Issue 1, Gilbertson and Page Ltd., Welwyn Garden City, USA, PMID 9368959, UI 98035434.

Sen, et al., Abstract of "Effect of *Quillaja saponaria* saponins and *Yucca schidigera* Plant Extract on Growth of *Escherichia coli*", Lett Appl Microbiol, Jul. 1998, pp. 35-38, vol. 27, Issue 1, Institute for Animal Production in the Tropics and Subtropics, University of Hohenheim, Stuttgart, Germany, PMID 9722995, UI 98390235.

Facey, P.C. et al., Investigation of Plants Used in Jamaican Folk Medicine for Anti-Bacterial Activity, J. Pharm. Pharmacol., (1999), pp. 1455-1460, vol. 51:12.

Farrington, E., Diaper Dermatitis, Pediatric Nursing, (1992), pp. 81-82, vol. 18:1.

Gnan, S.O. et al., Inhibition of *Staphylococcus aureus* by aueous Goiaba Extracts, Journal of Ethnopharmacology, (1999), pp. 103-108, vol. 68.

Janniger, C.K. et al., Diaper Dermatitis: An Approach to Prevention Employing Effective Diaper Care, Cutis, (1993), pp. 153-155, vol. 52.

Li, X-C et al., Antifungal Jujubogenin Saponins from *Colubrina retusa*, J. Nat. Prod., (1999), pp. 674-677, vol. 62:5.

Miyakoshi, M. et al., Antiyeast Steroidal Saponins from *Yucca schidigera* (Mohave Yucca), A New Anti-Food-Deteriorating Agent, J. Nat. Prod., (2000), pp. 332-338, vol. 63:3.

Nostro, A. et al., Extraction Methods and Bioautography for Evaluation of Medicinal Plant Antimicrobial Activity, Letters in Applied Microbiology, (2000), pp. 379-384, vol. 30.

Papadopoulou, K. et al., Compromised Disease Resistance in Saponin-Deficient Plants, Proceedings of the National Academy of Sciences of the U.S.A., (1999), pp. 12923-12928, vol. 96:22.

Sires, U.I. et al., Diaper Dermatitis, How to Treat and Prevent, Postgraduate Medicine, (1995), pp. 79-84, vol. 98:6.

Van Setten et al., Molecular Structures of Saponins from *Quillaja saponaria* Molina, Adv. Exp. Med. Biol., (1996), pp. 185-193, vol. 404.

Wong, D.L. et al., Diapering Choices: A Critical Review of the Issues, Pediatric Nursing, (1992), pp. 41-54, vol. 18:1.

*Yucca schidigera* printout from Geocites Website.

International Search Report from PCT/US2004/011043 dated Nov. 4, 2004.

* cited by examiner

ABSORBENT ARTICLE

BACKGROUND OF THE INVENTION

The present invention relates generally to absorbent articles such as diapers and more particularly to an absorbent article containing a urease inhibitor to reduce production of ammonia from urine.

Diaper rash is caused by several factors, one of which is prolonged exposure to moisture. Moisture is conducive to bacteria growth and promotes skin maceration and breakdown which allows the bacteria to infect the damaged skin. The occasional presence of feces which can include vast numbers of organisms further increases the potential for bacterial and fungal infection of damaged skin. Further, some bacteria produce ammonia through degradation of urine. Ammonia is used as a nutritional substrate by bacteria, resulting in growth of more bacteria and production of more ammonia in an increasing detrimental cycle. The production of ammonia also raises the pH of the skin. Normal skin pH is between about 4 and about 6.8. This range tends to inhibit bacterial growth. As pH increases, bacterial growth increases. Further, some enzymes contained in feces such as lipases and proteases which damage skin are more active at high pH. The skin can also be damaged by an increase in pH. Thus, the production of ammonia causes several detrimental effects which can lead to diaper rash.

Increases in ammonia also increase offensive odors which can be embarrassing particularly for incontinent adults. Thus, reduction of ammonia production from urine is advantageous for several reasons. Accordingly, there is a need for an absorbent article which reduces production of ammonia.

SUMMARY OF THE INVENTION

Briefly, an absorbent article of the present invention for absorbing body waste comprises a permeable liner having a body-facing surface oriented for facing a wearer when the absorbent article is worn and an absorbent-facing surface opposite the body-facing surface. The article also comprises an outer cover and an absorbent body positioned between the liner and the cover for absorbing body waste penetrating the liner. A *Yucca* sp. extract is positioned between the body-facing surface of the liner and the outer cover.

In another aspect, a method of the present invention inhibits production of ammonia from urine held adjacent a wearer's skin by an article. The method comprises applying a composition to the article. The composition includes a *Yucca* sp. extract.

Other features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

In accordance with the present invention, it has been discovered that compositions containing a *Yucca* sp. extract (hereinafter yucca extract), and more particularly *Yucca schidigera* are highly effective urease inhibitors (i.e., substances which inhibit production of ammonia from urine) when the compositions positioned in or are applied to an absorbent article.

The compositions of the present invention can be incorporated into a diaper, training pants, other child care products, infant care products, adult care products, feminine care products and the like having an improved ability to inhibit production of ammonia from urine. The present invention encompasses compositions, compositions as they are applied to absorbent articles, absorbent articles including compositions and methods of applying compositions to absorbent articles. The following detailed description will be made in the context of one type of absorbent article, a disposable diaper that is adapted to be worn by infants about their lower torso. It is readily apparent, however, that the absorbent article of the present invention would also be suitable for use as another type of absorbent article, such as a feminine care pad, an incontinence garment, training pants, prefastened or refastenable diaper pants, a wound dressing or a nursing pad. Further, the compositions of the invention are not limited to application on absorbent articles. For example, the compositions of the inventions could be used on skin-contacting substrates such as tissues, wet (pre-moistened) wipe materials and cosmetic pads (such as for cleansing or buffing).

Figure 1:
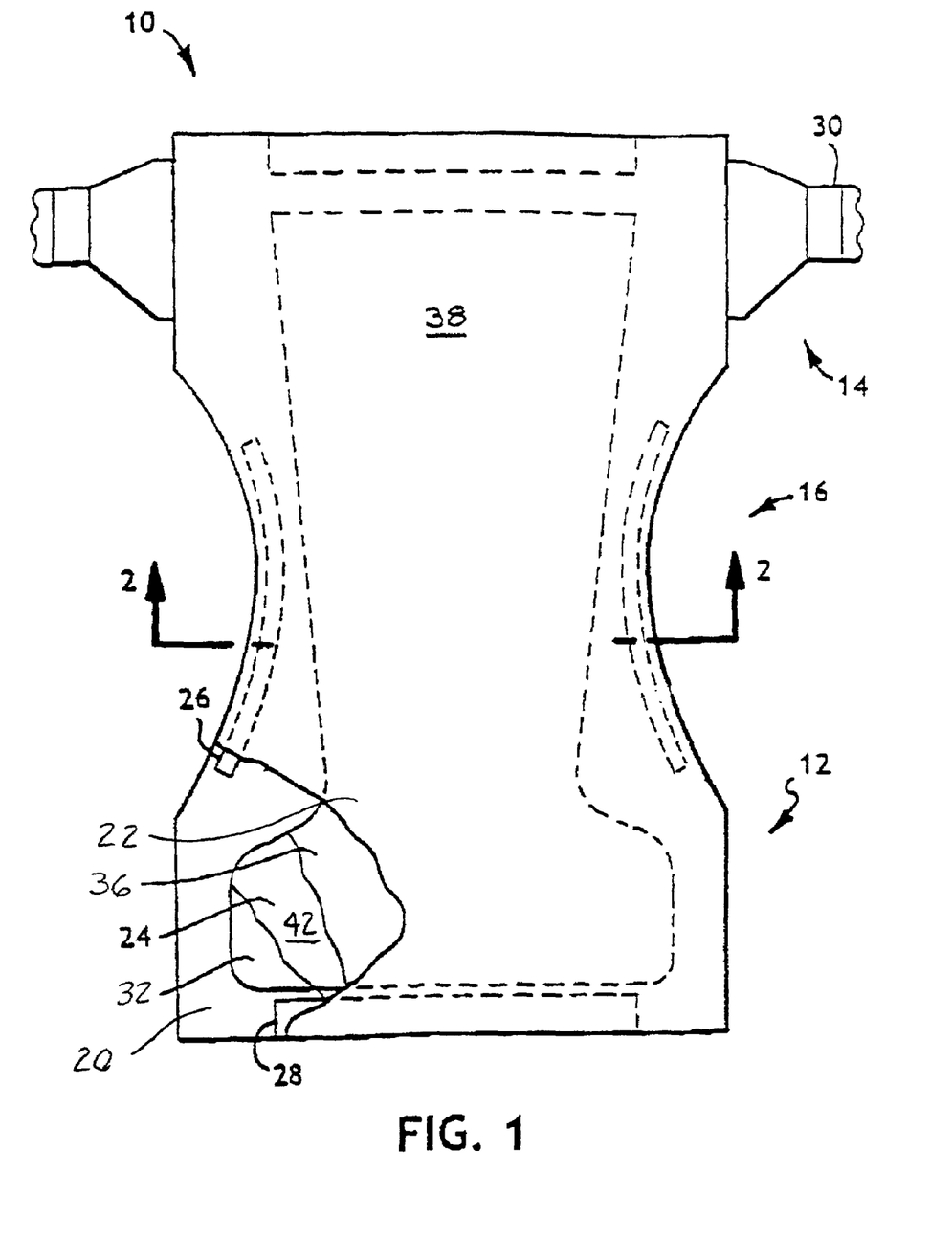
FIG. 1 is a schematic top plan in partial section of an absorbent article according to one aspect of the present invention.

Referring to the drawings and in particular to FIG. 1, a disposable diaper is designated in its entirety by the reference number 10. FIG. 1 schematically illustrates the disposable diaper 10 of the present invention in a flat-out, uncontracted state (i.e., with all elastic induced gathering and contraction removed). The diaper 10 generally comprises a front waist section 12, a rear waist section 14, and an intermediate section 16 interconnecting the front and rear waist sections 12, 14. The front and rear waist sections 12, 14 include the general portions of the diaper 10 adapted to extend substantially over the wearer's front abdominal region and the rear buttocks region, respectively, during use. The intermediate section 16 of the diaper 10 includes the general portion of the diaper 10 adapted to extend through the wearer's crotch region between the legs.

The diaper 10 includes a vapor permeable backsheet or outer cover 20, a liquid permeable topsheet or bodyside liner 22 positioned in facing relation with the outer cover 20, and an absorbent body 24, such as an absorbent pad, which is located between the outer cover 20 and the bodyside liner 22. The outer cover 20 has a length and a width coinciding with the length and width of the diaper 10. Generally, the absorbent body 24 has a length and width which are less than the length and width of the outer cover 20, respectively. Thus, marginal portions of the diaper 10, such as marginal sections of the outer cover 20, extend past the end edges and side edges of the absorbent body 24. Further, the bodyside liner 22 is generally coextensive with the outer cover 20 but may optionally cover an area larger or smaller than the area of the outer cover 20. In other words, the bodyside liner 22 is connected in superposed relation to the outer cover 20. While in use, the outer cover 20 is intended to face the garment and the bodyside liner 22 is intended to face the body of the wearer.

To provide improved fit and to help reduce leakage of body waste from the diaper 10, the diaper side margins and end margins may be elasticized with suitable elastic members, such as single or multiple strands of elastic. The elastic strands may be composed of natural or synthetic rubber and may optionally be heat shrinkable or heat elasticizable. For example, as representatively illustrated in FIG. 1, the diaper 10 may include leg elastics 26 which are constructed to operably gather and shirr the side margins of the diaper 10 to provide elasticized leg bands which can closely fit around the legs of the wearer to reduce leakage and provide improved comfort and appearance. Similarly, waist elastics 28 can be employed to elasticize the end margins of the diaper 10 to provide elasticized waists. The waist elastics 28 are configured to operably gather and shirr the waist sections to provide a resilient, comfortably close fit around the waist of the wearer. For clarity, the elastic members are illustrated in their uncontracted, stretched condition.

Fasteners, such as hook and loop fasteners 30, are provided to secure the diaper 10 on a wearer. Alternatively, other fasteners, such as buttons, pins, snaps, adhesive tape fasteners, cohesives, mushroom-and-loop fasteners, or the like, may be used. Additionally, more than two fasteners can be provided, particularly if the diaper 10 is to be provided prefastened. Further, the fasteners may vary in size and form without departing from the scope of the present invention.

Figure 2:
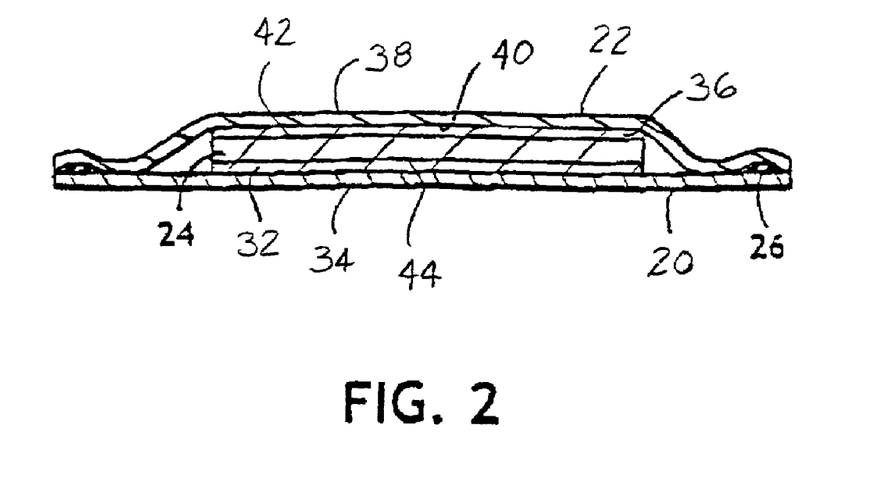
FIG. 2 is a schematic section of the absorbent article taken in the plane of line 2—2 of FIG. 1.

The diaper 10 may further include other layers between the absorbent body 24 and the bodyside liner 22 or outer cover 20. For example, as illustrated in FIGS. 1 and 2, the diaper 10 may include a ventilation layer 32 located between the absorbent body 24 and the outer cover 20 to insulate the outer cover 20 from the absorbent body 24 and improve air circulation to reduce the dampness of the garment facing surface or outer surface 34 of the outer cover 20. The ventilation layer 32 may also assist in distributing liquid waste to portions of the absorbent body 24 which do not directly receive the waste. The diaper 10 may also include a surge management layer 36 located between the bodyside liner 22 and the absorbent body 24 to prevent pooling of the liquid waste and further improve air exchange and distribution of the liquid waste within the diaper 10.

The diaper 10 may have various suitable shapes without departing from the scope of the present invention. For example, the diaper may have an overall rectangular shape, a T-shape, an hourglass shape or an I-shape as shown. Other suitable diaper components which may be incorporated in absorbent articles of the present invention include containment flaps, waist flaps, elastic side panels, and the like which are generally known to those skilled in the art. Likewise, if the diaper 10 is to be sold in a prefastened condition, the diaper 10 may have passive bonds (not shown) joining the rear waist section 14 to the front waist section 12.

Examples of diaper configurations suitable for use in connection with the instant application are described in U.S. Pat. No. 4,798,603 issued Jan. 17, 1989, in the name of Meyer et al. and entitled "ABSORBENT ARTICLE HAVING A HYDROPHOBIC TRANSPORT LAYER"; U.S. Pat. No. 5,176,668 issued Jan. 5, 1993, in the name of Bernardin and entitled "ABSORBENT STRUCTURE DESIGNED FOR ABSORBING BODY FLUIDS"; U.S. Pat. No. 5,176,672 issued Jan. 5, 1993, in the name of Bruemmer et al. and entitled "POCKET-LIKE DIAPER OR ABSORBENT ARTICLE"; U.S. Pat. No. 5,192,606 issued Mar. 9, 1993, in the name of Proxmire et al. and entitled "ABSORBENT ARTICLE HAVING A LINER WHICH EXHIBITS IMPROVED SOFTNESS AND DRYNESS, AND PROVIDES FOR RAPID UPTAKE OF LIQUID", and U.S. Pat. No. 5,509,915 issued Apr. 23, 1996 in the name of Hanson et al. and entitled "THIN ABSORBENT ARTICLE HAVING RAPID UPTAKE OF LIQUID", the disclosures of which are hereby incorporated by reference.

The components of the diaper 10 are assembled together using suitable attachment means, such as adhesive, sonic bonds, thermal bonds or combinations thereof. For example, the bodyside liner 22 and outer cover 20 may be assembled to each other and to the absorbent body 24 with lines of adhesive, such as a hot melt, pressure-sensitive adhesive. Similarly, other diaper components, such as the elastic members 26, 28, fastening members 30, and ventilation and surge layers 32, 36, respectively, may be attached to the diaper 10 using these the above-identified attachment means.

As further illustrated in FIG. 1, the outer cover 20 of the diaper 10 is made of a substantially vapor permeable material. The permeability of the outer cover 20 is selected to enhance the breathability of the diaper 10 and to reduce the hydration of the wearer's skin during use without allowing excessive condensation of vapor on an outer surface 34 (FIG. 2) of the outer cover 20 which can undesirably dampen the wearer's clothes. The outer cover 20 is generally constructed to be permeable to at least water vapor and has a water vapor transmission rate of at least about 1000 grams per square meter per day, desirably at least about 1500 grams per square meter per day, more desirably at least about 2000 grams per square meter per day, and even more desirably at least about 3000 grams per square meter per day. For example, the outer cover 20 may define a water vapor transmission rate between about 1000 grams per square meter per day and about 6000 grams per square meter per day. Materials having water vapor transmission rates less than those described above do not allow a sufficient amount of air exchange and undesirably result in increased levels of skin hydration.

Desirably, the outer cover 20 is substantially liquid impermeable. For example, the outer cover 20 may be constructed to provide a hydrohead value of at least about 60 centimeters, desirably at least about 80 centimeters, and more desirably at least about 100 centimeters when subjected to a hydrostatic pressure test. Materials which have hydrohead values less than those described above undesirably result in strike through of liquids, such as urine, during use. Such liquid strike through can undesirably result in a damp, clammy feeling on the outer cover 20 during use.

The outer cover 20 may be composed of any suitable materials which either directly provide the above described levels of liquid impermeability and air permeability or, in the alternative, materials which can be modified or treated in some manner to provide such levels. In one aspect, the outer cover 20 may be a nonwoven fibrous web constructed to provide the required level of liquid impermeability. For example, a nonwoven web made of spunbond or meltblown polymer fibers may be selectively treated with a water repellent coating or laminated with a liquid impermeable, vapor permeable polymer film to provide the outer cover 20. In one embodiment of the invention, the outer cover 20 includes a nonwoven web made of a plurality of randomly deposited hydrophobic thermoplastic meltblown fibers sufficiently bonded or otherwise connected to one another to provide a substantially vapor permeable and substantially liquid impermeable web. The outer cover 20 may also include a vapor permeable nonwoven layer which has been partially coated or otherwise configured to provide liquid impermeability in selected areas.

Examples of suitable materials for the outer cover 20 are also described in U.S. Pat. No. 5,482,765 issued Jan. 9, 1996, in the name of Bradley et al. and entitled "NONWOVEN FABRIC LAMINATE WITH ENHANCED BARRIER PROPERTIES"; U.S. Pat. No. 5,879,341 issued Mar. 9, 1999, in the name of Odorzynski et al. and entitled "ABSORBENT ARTICLE HAVING A BREATHABILITY GRADIENT"; U.S. Pat. No. 5,843,056 issued Dec. 1, 1998, in the name of Good et al. and entitled "ABSORBENT ARTICLE HAVING A COMPOSITE BREATHABLE BACKSHEET"; and U.S. patent application Ser. No. 08/882,712 filed Jun. 25, 1997, in the name of McCormack et al. and entitled "LOW GAUGE FILMS AND FILM/NONWOVEN LAMINATES", the disclosures of which are hereby incorporated by reference.

In one embodiment, the outer cover 20 is provided by a microporous film/nonwoven laminate material which includes a spunbond nonwoven material laminated to a microporous film. The spunbond nonwoven comprises filaments of about 1.8 denier extruded from a copolymer of ethylene with about 3.5 weight percent propylene and defines a basis weight between about 17 grams per square meter and about 25 grams per square meter. The film comprises a cast coextruded film having calcium carbonate particles therein and defines a basis weight of about 58 grams per square meter prior to stretching. The film is preheated, stretched and annealed to form the micropores and then laminated to the spunbond nonwoven. The resulting microporous film/nonwoven laminate based material has a basis weight between about 30 grams per square meter and about 60 grams per square meter and a water vapor transmission rate of between about 3000 grams per square meter per day and about 6000 grams per square meter per day. Examples of such film/nonwoven laminate materials are described in more detail in U.S. patent application Ser. No. 08/882,712 filed Jun. 25, 1997, in the name of McCormack et al. and entitled "LOW GAUGE FILMS AND FILM/NONWOVEN LAMINATES", the disclosure of which has been incorporated by reference.

It is also envisioned that the outer cover 20 may be formed from an extensible material without departing from the scope of the present invention. Extensible and stretchable outer cover materials can be used in absorbent articles to provide various benefits including better fitting articles.

As illustrated in FIG. 2, the bodyside liner 22 includes a body-facing surface 38 oriented for facing the wearer when the absorbent article 10 is worn and an absorbent-facing surface 40 opposite the body-facing surface. The bodyside liner 22 is intended to isolate the wearer's skin from liquids held in the absorbent body 24. Desirably, the body-facing surface 38 is compliant, soft feeling, and nonirritating to the wearer's skin. Further, the bodyside liner 22 is desirably less hydrophilic than the absorbent body 24, to present a relatively dry surface to the wearer, and sufficiently porous to be liquid permeable, permitting liquid to readily penetrate through its thickness. A suitable bodyside liner 22 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers.

Various woven and nonwoven fabrics can be used for the bodyside liner 22. For example, the bodyside liner 22 may be composed of a meltblown or spunbond web of polyolefin fibers. The bodyside liner 22 may also be a bonded-carded web composed of natural and/or synthetic fibers. The bodyside liner 22 may be composed of a substantially hydrophobic material, and the hydrophobic material may, optionally, be treated with a surfactant or otherwise processed to impart a desired level of wettability and/or hydrophilicity. In a particular aspect of the present invention, the bodyside liner 22 comprises a nonwoven, spunbond, polypropylene fabric composed fibers having between about 2.8 denier and about 3.2 denier formed into a web having a basis weight of about 22 grams per square meter and a density of about 0.06 gram per cubic centimeter.

In one embodiment of the present invention, the bodyside liner 22 may be surface treated with about 0.3 weight percent of a surfactant mixture that contains a mixture of AHCOVEL Base N-62 and GLUCOPON 220UP surfactants in about a 3:1 ratio based on a total weight of the surfactant mixture. The AHCOVEL Base N-62 surfactant includes a blend of hydrogenated ethoxylated castor oil and sorbitan monooleate in a 55:45 weight ratio and may be purchased from Hodgson Textile Chemicals Inc. of Mount Holly, N.C. The GLUCOPON 220UP surfactant includes alkyl polyglycoside and may be purchased from Henkel Corporation. The surfactant may include additional ingredients such as aloe. The surfactant may be applied by any conventional means, such as spraying, printing, brush coating or the like. The surfactant may be applied to the entire bodyside liner 22 or may be selectively applied to particular sections of the bodyside liner 22, such as medially along a longitudinal centerline of the diaper, to provide greater wettability of these sections.

In one embodiment, the absorbent body 24 of the diaper 10 comprises a matrix of hydrophilic fibers, such as a web of cellulosic fluff, mixed with particles of a high-absorbency material commonly known as superabsorbent material. In one particular embodiment, the absorbent body 24 includes a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. Alternatively, the absorbent body 24 may include a laminate of fibrous webs and superabsorbent material or other suitable matrix for maintaining a superabsorbent material in a localized area.

The absorbent body 24 may have any of a number of shapes. For example, the absorbent body 24 may be rectangular, I-shaped, or T-shaped. It is generally desirably for the absorbent body 24 to be narrower in the intermediate section 16 than in the front and rear waist sections 12, 14 of the diaper 10. The absorbent body 24 may comprise a single layer or, in the alternative, may comprise multiple layers, all of which need not extend the entire length and width of the absorbent body 24. In one embodiment of the invention, the absorbent body 24 is generally T-shaped and has a longitudinal center portion and laterally extending portions which generally correspond to the front waist section 12 of the absorbent article for improved performance, especially for male infants. Although the absorbent body 24 may have other dimensions without departing from the scope of the present invention, in one embodiment the front waist section 12 of the article has a lateral width of about 18 centimeters, the narrowest portion of the intermediate section 16 has a width of about 7.5 centimeters and the rear waist section 14 has a width of about 11.4 centimeters. As will be appreciated by those skilled in the art, the size and the absorbent capacity of the absorbent body 24 may be varied to accommodate wearers ranging from infants to adults. In addition, the densities and/or basis weights of the absorbent body 24 may be varied. In one embodiment, the absorbent body 24 has an absorbent capacity of at least about 300 grams of synthetic urine.

In embodiments in which the absorbent body 24 has the combination of hydrophilic fibers and high-absorbency particles, the hydrophilic fibers and high-absorbency particles desirably have an average basis weight between about 400 grams per square meter and about 900 grams per square meter. More desirably, the average composite basis weight of the absorbent body 24 is between about 500 grams per square meter and about 800 grams per square meter, and still more desirably between about 550 grams per square meter and about 750 grams per square meter to provide the desired performance.

Further, the absorbent body 24 has a bulk thickness less than about 0.6 centimeters. Desirably, the bulk thickness is less than about 0.53 centimeters, and more desirably less than about 0.5 centimeters to provide improved benefits. The bulk thickness is determined under a restraining pressure of 1.38 kilo Pascals.

The high-absorbency material may be selected from natural, synthetic, and modified natural polymers and materials. The high-absorbency materials may be inorganic materials, such as silica gels, or organic compounds, such as crosslinked polymers. The term "crosslinked" refers to methods for effectively rendering normally water-soluble materials substantially water insoluble but swellable. Such methods include, for example, physical entanglement, crystalline domains, covalent bonds, ionic complexes and associations, hydrophilic associations such as hydrogen bonding, and hydrophobic associations or Van der Waals forces.

Examples of suitable synthetic, polymeric, high-absorbency materials include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinyl morpholinone), poly(vinyl alcohol), and mixtures and copolymers thereof. Further polymers suitable for use in the absorbent body 24 include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and the like. Mixtures of natural and wholly or partially synthetic absorbent polymers may also be useful in the present invention.

The high absorbency material may be in any of a wide variety of geometric forms. As a general rule, it is desirably that the high absorbency material be in the form of discrete particles. However, the high absorbency material may also be in the form of fibers, flakes, rods, spheres, needles, or the like. In general, the high absorbency material is present in the absorbent body 24 in an amount between about 5 weight percent and about 90 weight percent, desirably in an amount of at least about 30 weight percent, and even more desirably in an amount of at least about 50 weight percent based on a total weight of the absorbent body 24. For example, in one particular embodiment, the absorbent body 24 may include a laminate which having at least about 50 weight percent and desirably at least about 70 weight percent of high-absorbency material overwrapped by a fibrous web or other suitable material for maintaining the high-absorbency material in a localized area.

An example of high-absorbency material suitable for use in the present invention is SANWET IM 3900 polymer available from Hoechst Celanese of Portsmouth, Va. Other suitable superabsorbents may include FAVOR SXM 880 polymer obtained from Stockhausen of Greensboro, N.C.

Optionally, a substantially hydrophilic tissue wrapsheet (not shown) may be used to help maintain the integrity of the structure of the absorbent body 24. The tissue wrapsheet is typically placed around the absorbent body 24 over at least the two major facing surfaces thereof. The tissue wrapsheet may be composed of an absorbent cellulosic material, such as creped wadding or a high wet-strength tissue. In one embodiment of the invention, the tissue wrapsheet is configured to provide a wicking layer which helps to rapidly distribute liquid over the mass of absorbent fibers constituting the absorbent body 24.

The absorbent body 24 of the present invention may also include a plurality of zones of high air permeability which allow air and vapors to readily pass through the absorbent body 24, through the vapor permeable outer cover 20 and out of the diaper 10 into ambient air. For example, the absorbent body 24 may include a plurality of air passageways providing the absorbent body 24 with zones or regions of high air permeability. The portions of the absorbent body 24 adjacent the air passageways provide zones or regions of high absorption. The zones of high air permeability are designed to provide maximum air exchange from the absorbent body 24 while the zones of high absorption are designed to receive and hold the majority of the body waste. The absorbent body 24 may define any number of zones of high air permeability which provide improved air exchange. Desirably, the absorbent body 24 has at least about three and more desirably at least about five different zones of high air permeability for improved performance.

The zones of high air permeability, such as the air passageways, are configured to enhance the breathability of the article to reduce the hydration of the wearer's skin during use without allowing excessive condensation of vapor on the garment facing surface 34 of the outer cover 20. Such condensation of vapor on the garment facing surface 34 of the diaper 10 can undesirably dampen the wearer's clothes. The zones of high air permeability are generally located in the area of the diaper over which air and vapor can transfer from the bodyside liner 22, through the absorbent body 24 and any other intervening layer or layers of material, and out the vapor permeable outer cover 20. For example, the zones of high air permeability may be located throughout the entire absorbent body 24 or may be selectively located in regions of the absorbent body 24 which provide the maximum air exchange, such as the intermediate section 16 of the diaper 20. In one particular embodiment, the zones of high air permeability are located in the front and intermediate sections 12, 16, respectively, of the diaper 10 for improved air exchange.

The zones of high absorption, on the other hand, are not designed to transfer high levels of air and vapor from the interior of the diaper 10. Thus, the air exchange from the bodyside liner 22 of the diaper 10 to the outer cover 20 of the diaper and into the ambient surroundings occurs generally through the absorbent body 24 in the zones of high air permeability. Some air exchange through the absorbent body 24 may also occur to a limited degree in the zones of high absorption. The zones of high air permeability may have any desired configuration including rectangular, circular, hourglass, oval, and the like, and may also include selected longitudinal or lateral strips or multiple regions which may be intermittently located.

The zones of high air permeability may have any desired dimensions which effectively provide improved air exchange while preventing excessive condensation of vapor from the absorbent body 24 through and onto the garment facing surface 34 of the outer cover 20. Desirably, the zones of high air permeability may define a total area between about 5 percent and about 75 percent, more desirably at least about 10 percent, even more desirably between about 10 and about 70 percent, and still more desirably between about 10 and about 60 percent of the total surface area of the absorbent body 24 of the diaper 10. For example, in a diaper 10 intended for use on a medium sized infant, the zones of high air permeability may define a total area between about 6 and about 90 square centimeters.

When the total area of the zones of high air permeability is greater than the above amounts, the diaper 10 may exhibit an undesirable amount of condensation of vapor on the exposed, garment facing surface 34 of the outer cover 20 undesirably resulting in a clammy feeling on the garment facing surface. Whereas, when the total area of the zones of high air permeability is less than the above amounts, the diaper 10 may exhibit a low level of air exchange resulting in high levels of skin hydration which can undesirably lead to skin irritation and rash.

The zones of high air permeability of the absorbent body 24 of the diaper 10 are constructed to be substantially permeable to at least air and preferably permeable to water vapor. For example, the zones of high air permeability of the absorbent body 24 define a Frazier Porosity value which is at least about 10 percent, more desirably at least about 20 percent and even more desirably at least about 50 percent greater than the Frazier Porosity value of the zones of high absorption of the absorbent body 24. The Frazier Porosity values can be determined using a Frazier Air Permeability Tester available from Frazier Precision Instrument Co. of Gaithersburg, Md. and Method 5450, Federal Test Methods Standard No. 191A. For the purposes of the present invention, the test is conducted with a sample measuring about 20.3 centimeters by about 20.3 centimeters. When the zones of high air permeability exhibit Frazier Porosity values less than those indicated above, the diaper 10 may exhibit a low level of air exchange resulting in high levels of skin hydration which can undesirably lead to skin irritation and rash.

The zones of high air permeability may be provided in a variety of ways. The zones of high air permeability may be integral portions of the absorbent body 24 of the absorbent article or may be provided by apertures, holes or open spaces in the absorbent body 24. For example, portions of the absorbent body 24 may be discontinuous or removed to provide the zones. Alternatively, the zones of high air permeability may be provided by portions of the absorbent body 24 constructed to absorb less liquid waste thereby resulting in improved air flow through such portions in use. For example, portions of the absorbent body 24 may be void of or contain substantially less high-absorbency material than other portions of the absorbent body 24 to provide improved air flow. Portions of the absorbent body 24 may otherwise be treated or coated with a solution rendering them hydrophobic to provide the zones of high air permeability in selected areas. In other alternative configurations, the zones of high air permeability may be provided by creating voids or holes in the absorbent body 24 and placing other materials having a higher air permeability than the absorbent body 24, such as those materials described below as being suitable for the surge management layer 36, in the holes or voids.

Due to the thinness of absorbent body 24 and the high absorbency material within the absorbent body 24, the liquid uptake rates of the absorbent body 24, by itself, may be too low, or may not be adequately sustained when liquid is introduced several times into the absorbent body 24. To improve the overall liquid uptake and air exchange, the diaper 10 of the present invention may further include a porous, liquid-permeable layer of surge management material 36, as illustrated in FIG. 1. The surge management layer 36 is typically less hydrophilic than the absorbent body 24, and has an operable level of density and basis weight to quickly collect and temporarily hold liquid surges, to transport the liquid from its initial entrance point and to substantially completely release the liquid to other parts of the absorbent body 24. This configuration can help prevent the liquid from pooling and collecting on the portion of the diaper 10 positioned against the wearer's skin, thereby reducing the feeling of wetness by the wearer. The structure of the surge management layer 36 also generally enhances the air exchange within the diaper 10.

Various woven and nonwoven fabrics can be used to construct the surge management layer 36. For example, the surge management layer 36 may be a layer composed of a meltblown or spunbond web of synthetic fibers, such as polyolefin fibers. The surge management layer 36 may also be a bonded-carded-web or an airlaid web composed of natural and synthetic fibers. The bonded-carded-web may, for example, be a thermally bonded web which is bonded using low melt binder fibers, powder or adhesive. The webs can optionally include a mixture of different fibers. The surge management layer 36 may be composed of a substantially hydrophobic material, and the hydrophobic material may optionally be treated with a surfactant or otherwise processed to impart a desired level of wettability and hydrophilicity. In one particular embodiment, the surge management layer 36 includes a hydrophobic, nonwoven material having a basis weight between about 30 grams per square meter and about 120 grams per square meter.

For example, in one particular embodiment, the surge management layer 36 includes a bonded-carded-web, nonwoven fabric having bicomponent fibers and an overall basis weight of about 83 grams per square meter. The surge management layer 36 in such a configuration can be a homogeneous blend composed of about 60 weight percent polyethylene/polyester (PE/PET), sheath-core bicomponent fibers having a fiber denier of about 3 d and about 40 weight percent single component polyester fibers having a fiber denier of about 6 d and fiber lengths between about 3.8 and about 5.08 centimeters.

In the illustrated embodiment, the surge management layer 36 is arranged in a direct, contacting liquid communication with the absorbent body 24. The surge management layer 36 may be operably connected to the bodyside liner 22 with a conventional pattern of adhesive, such as a swirl adhesive pattern. In addition, the surge management layer 36 may be operably connected to the absorbent body 24 with a conventional pattern of adhesive. The amount of adhesive should be sufficient to provide the desired levels of bonding, but should be low enough to avoid excessively restricting the movement of liquid from the bodyside liner 22, through the surge management layer 36 and into the absorbent body 24.

The absorbent body 24 is positioned in liquid communication with surge management layer 36 to receive liquids released from the surge management layer 36, and to hold and store the liquid. The surge management layer 36 serves to quickly collect and temporarily hold discharged liquids, to transport such liquids from the point of initial contact and spread the liquid to other parts of the surge management layer 36, and then to substantially completely release such liquids into the layer or layers constituting the absorbent body 24.

The surge management layer 36 can be of any desired shape. Suitable shapes include for example, circular, rectangular, triangular, trapezoidal, oblong, dog bone, hourglass, or oval. In the illustrated embodiment, the surge management layer 36 is coextensive with the absorbent body 24. Alternatively, the surge management layer 36 may extend over only part of the absorbent body 24. Where the surge management layer 36 extends only partially along the length of the absorbent body 24, the surge management layer 36 may be selectively positioned anywhere along the absorbent body 24. For example, the surge management layer 36 may function more efficiently when it is offset toward the front waist section 12 of the diaper 10. The surge management layer 36 may also be laterally centered on the absorbent body 24.

Additional materials suitable for the surge management layer 36 are set forth in U.S. Pat. No. 5,486,166 issued Jan. 23, 1996, in the name of C. Ellis et al. and entitled "FIBROUS NONWOVEN WEB SURGE LAYER FOR PERSONAL CARE ABSORBENT ARTICLES AND THE LIKE"; U.S. Pat. No. 5,490,846 issued Feb. 13, 1996, in the name of Ellis et al. and entitled "IMPROVED SURGE MANAGEMENT FIBROUS NONWOVEN WEB FOR PERSONAL CARE ABSORBENT ARTICLES AND THE LIKE"; and U.S. Pat. No. 5,364,382 issued Nov. 15, 1994, in the name of Latimer et al. and entitled "ABSORBENT STRUCTURE HAVING IMPROVED FLUID SURGE MANAGEMENT AND PRODUCT INCORPORATING SAME", the disclosures of which are hereby incorporated by reference.

As illustrated in FIG. 1, the diaper 10 may also include a ventilation layer 32 located between the outer cover 20 and the absorbent body 24. The ventilation layer 32 serves to facilitate movement of air within and through the diaper 10 and prevent the outer cover 20 from being in direct contact with at least a portion of the absorbent body 24. Specifically, the ventilation layer 32 serves as a conduit through which air and water vapor can move from the absorbent body 24 through the vapor permeable outer cover 20.

The ventilation layer 32 may be formed from materials described above as being suitable for the surge management layer 36 such as nonwoven, (e.g., spunbond, meltblown or carded), woven, or knitted fibrous webs composed of natural fibers and/or synthetic polymeric fibers. Suitable fibers include, for example, acrylic fibers, polyolefin fibers, polyester fibers, or blends thereof. The ventilation layer 32 may also be formed from a porous foam material such as an open-celled polyolefin foam, a reticulated polyurethane foam, and the like. The ventilation layer 32 may include a single layer of material or a composite of two or more layers of material. In a particular aspect, the ventilation layer 32 includes a hydrophobic, nonwoven material having a thickness of at least about 0.10 centimeters determined under a restraining pressure of 0.34 kilo Pascal and a basis weight between about 20 grams per square meter and about 120 grams per square meter. For example, the ventilation layer 32 may comprise a bonded-carded-web, nonwoven fabric including bicomponent fibers and having an overall basis weight of about 83 grams per square meter. The ventilation layer 32 in such a configuration can be a homogeneous blend composed of about 60 weight percent polyethylene/polyester (PE/PET), sheath-core bicomponent fibers having a fiber denier of about 3 d and about 40 weight percent single component polyester fibers having a fiber denier of about 6 d and having fiber lengths between about 3.8 and about 5.08 centimeters.

The ventilation layer 32 can be of any desired shape. Suitable shapes include for example, circular, rectangular, triangular, trapezoidal, oblong, dog bone, hourglass, or oval. The ventilation layer 32 may extend beyond, completely over or partially over the absorbent body 24. For example, the ventilation layer 32 may suitably be located over the intermediate section 16 of the diaper 10 and be substantially laterally centered. It is generally desired that the entire absorbent body 24 be overlaid with the ventilation layer 32 to prevent substantially all direct contact between the outer cover 20 and the absorbent body 24. In the illustrated embodiment, the ventilation layer 32 is coextensive with the absorbent body 24, allowing for maximum air exchange with minimal dampness on the garment facing surface 34 of the outer cover 20.

In the illustrated embodiment, the ventilation layer 32 directly contacts the absorbent body 24. The ventilation layer 32 may be operably connected to the outer cover 20 with a conventional pattern of adhesive, such as a swirl adhesive pattern. In addition, the ventilation layer 32 may be operably connected to the absorbent body 24 with a conventional pattern of adhesive. The amount of adhesive should be sufficient to provide the desired levels of bonding, but should be low enough to avoid excessively restricting the movement of air and vapor from the absorbent body 24 and through the outer cover 20.

The ventilation layer 32 may further serve to quickly collect and temporarily hold discharged liquids, which pass through the absorbent body 24 and, in particular, through the zones of high air permeability within the absorbent body 24. The ventilation layer 32 may then transport such liquids from the point of initial contact and spread the liquid to other parts of the ventilation layer 32, and then substantially completely release such liquids into the layer or layers of the absorbent body 24.

In one embodiment, a composition may be applied to the body-facing surface 38 of the bodyside liner 22 of the diaper 10 to protect the barrier of the skin covered by the diaper. Such a composition may generally include emollient(s), viscosity enhancer(s) and extracted botanical active(s). The composition can also include natural fats or oils, solidifying agents and sterols or sterol derivatives. Additionally, the composition can include a rheology modifier and a natural clay or a synthetic analog of a natural clay. For example, the compositions of the invention may include between about 50 weight percent and about 95 weight percent of one or more emollients; between about 0.1 weight percent and about 40 weight percent of one or more viscosity enhancers; and between about 0.1 weight percent and about 10 weight percent of one or more extracted botanical actives. The composition may include other ingredients as well. Ranges are used to describe the relative amounts of components in the compositions of the invention as well as to describe the relative physical properties of the compositions. These ranges are illustrative and one of skill in the art will recognize that the nature of the composition will dictate the various levels of components which must be used to achieve the intended benefit for the skin barrier. The levels can be determined by routine experimentation in view of the disclosure provided herein.

The compositions of the invention can be in a variety of physical forms including emulsions, lotions, creams, ointments, salves, suspensions, gels or hybrids thereof.

The emollients of the compositions act as lubricants to reduce the abrasiveness of the bodyside liner 22 to the skin and, upon transfer to the skin, help to maintain the soft, smooth and pliable nature of the skin. In general, emollients are skin-conditioning ingredients which help to soften, smooth, plasticize, lubricate, moisturize, improve the appearance of, improve the feel of and protect skin. Suitable emollients which can be incorporated into the compositions include oils such as petroleum based oils, petrolatum, vegetable based oils, hydrogenated vegetable oils, animal oils, hydrogenated animal oils, mineral oils, natural or synthetic oils, alkyl dimethicones, alkyl methicones, alkyldimethicone copolyols, phenyl silicones, siliconized waxes, alkyl trimethylsilanes, dimethicone, lanolin and its derivatives, esters, branched esters, glycerol esters and derivatives, propylene glycol esters and derivatives, alkoxylated carboxylic acids, alkoxylated alcohols, fatty alcohols, triglycerides, alkyl hydroxystearates and mixtures of such compounds. The esters can be selected from cetyl palmitate, stearyl palmitate, cetyl stearate, isopropyl laurate, isopropyl myristate, isopropyl palmitate, behenyl behenate, stearyl behenate, C12–C15 alkyl fumarate, C20–C40 alkyl behenate, dibehenyl fumarate, branched esters and mixtures thereof. Ethers such as eucalyptol, cetearyl glucoside, dimethyl isosorbicide polyglyceryl-3 cetyl ether, polyglyceryl-3 decyltetradecanol, propylene glycol myristyl ether and mixtures thereof can also be used as emollients. The fatty alcohols include octyldodecanol, lauryl, myristyl, cetyl, stearyl and behenyl alcohol, C24 and greater fatty alcohols and mixtures thereof. One a particularly well suited emollient is petrolatum. Other conventional emollients may also be added in a manner that maintains the desired properties of the compositions set forth herein.

To provide improved stability and transfer to the skin of the wearer, the compositions may include between about 1 and about 95 weight percent, desirably between about 20 weight percent and about 75 weight percent, and more desirably between about 40 weight percent and about 60 weight percent of the emollient. In particular embodiments, the emollient can constitute at least about 1 weight percent. The emollient can alternatively be at least about 20 percent, and optionally, can be at least about 40 percent to provide improved performance. In other aspects, the emollient can be less than about 95 weight percent. The emollient can alternatively be not more than about 75 percent, and optionally, can be not more than about 60 percent to provide improved effectiveness. Compositions including an amount of emollient greater than the described amounts tend to have lower viscosities which undesirably lead to migration of the composition. Whereas, compositions including an amount of emollient less than the described amounts tend to provide less transfer to the wearer's skin.

The solidifying agent(s) in the compositions of the present invention primarily functions to solidify the composition so that the composition is a solid at room temperature and has a penetration hardness of at least 5 millimeters and has a melting point of at least 32 degrees Celsius. The solidifying agent may also provide a tackiness to the composition which improves the transfer by adhesion to the skin of the wearer. Depending on the solidifying agent selected, the solidifying agent can also modify the mode of transfer so the composition tends to fracture or flake off instead of actually rubbing off onto the skin of the wearer which can lead to improved transfer to the skin. The solidifying agent may further function as an emollient, occlusive agent, moisturizer, barrier enhancer, viscosity enhancer and combinations thereof. The solidifying agents may include waxes as well as compounds which functionally perform as waxes.

The solidifying agents can be selected from alkyl siloxanes, polymers, hydrogenated vegetable oils having a melting point of 35 degrees Celsius or greater, fatty acid esters and branched esters with a melting point of 35 degrees Celsius or greater, alkyl hydroxystearates (>C16), alkoxylated alcohols and alkoxylated carboxylic acid. Additionally, the solidifying agents can be selected from animal, vegetable and mineral waxes, synthetic waxes and alkyl silicones. Examples of solidifying agents include, but are not limited to, the following: alkyl silicones, alkyl trimethylsilanes, beeswax, behenyl behenate, behenyl benzoate, C24–C28 alkyl dimethicone, C30 alkyl dimethicone, cetyl methicone, stearyl methicone, cetyl dimethicone, stearyl dimethicone, cerotyl dimethicone, candelilla wax, carnauba, synthetic carnauba, PEG-12 carnauba, cerasin, hydrogenated microcrystalline wax, jojoba wax, microcrystalline wax, lanolin wax, ozokerite, paraffin, synthetic paraffin, cetyl esters, behenyl behenate, C20–C40 alkyl behenate, C12–C15 lactate, cetyl palmitate, stearyl palmitate, isosteryl behenate, lauryl behenate, stearyl benzoate, behenyl isostearate, cetyl myristate, cetyl octanoate, cetyl oleate, cetyl ricinoleate, cetyl stearate, decyl oleate, di-C12–C15 alkyl fumerate, dibehenyl fumerate, myristyl lactate, myristyl lignocerate, myristyl myristate, myristyl stearate, lauryl stearate, octyldodecyl stearate, octyldodecyl stearoyl stearate, oleyl arachidate, oleyl stearate, tridecyl behenate, tridecyl stearate, tridecyl stearoyl stearate, pentaerythrityl tetrabehenate, pentaerythritylhydrogenated rosinate, pentaerythrityl distearate, pentaerythrityl tetraabeite, pentaerythrityl tetracocoate, pentaerythrityl tetraperlargonate, pentaerythrityl tetrastearate, ethylene vinyl acetate, polyethylene, hydrogenated cottonseed oil, hydrogenated vegetable oil, hydrogenated squalene, hydrogenated coconut oil, hydrogenated jojoba oil, hydrogenated palm oil, hydrogenated palm kernel oil, hydrogenated olive oil, polyamides, metal stearates and other metal soaps, C30–C60 fatty alcohols, C20+ fatty amides, polypropylene, polystyrene, polybutane, polybutylene terephthalate, polydipentane, polypropylene, zinc stearate, dodecyl laurate, stearyl palmitate, octadecyl hexadecanoate, octadecyl palmitate, stearyl behenate, docosyl octanoate, tetradecyl-octadecanyl behenate, hexadecyl-cosanyl hexacosanate, shellac wax, glycol montanate, fluoranated waxes, C20–C40 alkyl hydroxystearyl stearate and mixtures of such compounds. Suitable branched esters include tetradecyl-octadecanyl behenate and hexadecyl-cosanyl-hexacosanate. In one aspect, the solidifying agent is a blend including about 70 weight percent cerasin wax, about 10 weight percent microcrystalline wax, about 10 weight percent paraffin wax and about 10 weight percent cetyl esters (synthetic spermaceti wax).

Further, the absorbent articles of the present invention include urease inhibiting compositions comprising an amount of yucca extract sufficient to provide urease inhibiting activity. A suitable amount of yucca extract is at least about 0.001 weight percent, and more desirably at least about 0.01 weight percent based on the total weight of the composition applied to the absorbent article. Further, the amount of yucca extract should be small enough to prevent undesirable coloration of the absorbent article. Desirably, the amount of yucca extract is less than about 1.0 weight percent based on total weight of the composition. Although other yucca extracts may be used without departing from the scope of the present invention, in one embodiment the yucca extract comprises *Yucca schidigera*, and more particularly, a *Yucca schidigera* solution sold under the trade designation Yucca 70 by Sher-Mar Enterprises of Poway, Calif.

Although the yucca extract may be positioned in other locations in the absorbent article without departing from the scope of the present invention, in one embodiment the extract is positioned between the body-facing surface 38 of the liner 22 and the outer cover 20 to prevent direct contact between the extract and the skin of the wearer. Thus positioned, the moisture of the skin will be less likely to activate the extract prematurely. In one particular embodiment, the yucca extract is applied to the absorbent-facing surface 40 of the liner 22. Alternatively, it is envisioned that the yucca extract may be held within the absorbent body 24. For example, the extract may be held between the opposite outer faces 42, 44 (FIG. 2) of the body 24 and/or it may be applied to at least one of the faces of the absorbent body.

As will be appreciated by those skilled in the art, the previously described urease inhibiting compositions may be applied to the absorbent article before the article is positioned around the wearer to inhibit production of ammonia from urine. Although other amounts may be applied without departing from the scope of the present invention, in one embodiment at least about 0.001 weight percent, and more desirably at least about 0.01 weight percent based on the total weight of the composition. Further, the amount of yucca extract should be small enough to prevent undesirable coloration of the composition. Desirably, the amount of yucca extract is less than about 1.0 weight percent based on total weight of the composition. The yucca extract may be applied using any conventional process such as printing or slot coating. Desirably, the yucca extract applied to the article includes at least about 0.001 weight percent of *Yucca schidigera*, and more desirably at least about 0.01 weight percent of *Yucca schidigera* based on the total weight of the composition and less than about 1.0 weight percent of *Yucca schidigera*.

The present invention is illustrated by the following examples which are merely for the purpose of illustration and is not to be regarded as limiting the scope of the invention or manner in which it may be practiced.

EXAMPLE 1

Various commercially available yucca extracts used for animal feed supplements were tested to determine their urease inhibiting efficacy. Two milliliters (ml) of the respective yucca extract, 18 ml of urine and 2 ml of jack bean urease (10 milligrams/milliliter (mg/ml)) were placed in a 50 ml conical tube. The jack bean urease was obtained from Sigma Chemical Company of St. Louis, Mo., and identified as U-4002. The final concentration of jack bean urease used was 0.91 mg/ml (1.0 mg jack bean urease=1000 U). The tube was capped and the contents vigorously mixed with a vortex. After a two hour incubation period at 25 degrees Celsius, the ammonia in gas phase above the mixture was analyzed using a Gastec® ammonia detection tube available from Gastec Corporation of Ayase-shi Kanagawa-ken, Japan. A control mixture containing 2 ml of de-ionized water, 18 ml of urine and 2 ml of jack bean urease was also analyzed.

Four yucca extracts which were tested included 100% pure *Yucca schidigera* powder sold under the trade designation Desert Pure Yucca by Sher-Mar Enterprises of Poway, Calif., a *Yucca schidigera* solution sold under the trade designation Yucca 70 by Sher-Mar Enterprises, 50% food grade yucca powder sold under the product code YUCEXT50 by Garuda International, Inc. of Lemon Cove, Calif., and a yucca powder sold under the trade designation Dinase-30-dry by Diversified Nutri-Agri Technologies, Inc. of Gainesville, Ga. The Desert Pure Yucca and the Dinase-30-dry yucca powders exhibited low apparent urease inhibiting activity. The 50% food grade yucca exhibited medium apparent urease inhibiting activity, and the Yucca 70 exhibited high apparent urease inhibiting activity. Specific results are shown in Table 1.

TABLE 1

| Yucca Extract | Extract Concentration | Ammonia Measured (ppm) | % Inhibition of Released Ammonia |
| --- | --- | --- | --- |
| None | — | 780 | — |
| Dinase-30-dry | 0.9 mg/ml | 620 | 20.5 |
| Yucca 70 | 9.1% | 130 | 83.3 |
| 100% pure *Yucca schidigera* powder | 0.9 mg/ml | 740 | 5.1 |
| 50% food grade yucca powder | 0.5 mg/ml | 600 | 23.1 |

EXAMPLE 2

Various concentrations of *Yucca schidigera* extract were studied to determine their urease inhibiting efficacy. An amount of a *Yucca schidigera* solution sold under the trade designation Yucca 70 by Sher-Mar Enterprises was thoroughly mixed in a vortex with 18 ml of urine and 2 ml of jack bean urease. After a 2 hour incubation period at 25 degrees Celsius, the resulting mixture was analyzed with an ammonia detection tube. A control mixture containing only 18 ml of urine, 2 ml of de-ionized water and 2 ml of jack bean urease was also analyzed.

The results of the mixtures containing the yucca extract were compared to the control mixture. The final concentrations of the yucca extract analyzed were zero weight percent per volume (control mixture), 0.9 percent, 4.6 percent, and 9.1 percent. The 0.9 percent mixture containing 6.3 milligrams of yucca extract solids per milliliter of urine demonstrated about 54 percent reduction in gas phase ammonia from the control mixture. The 4.6 percent mixture containing 31.5 milligrams of yucca extract solids per milliliter of urine and the 9.1 percent mixture containing 63 milligrams of yucca extract solids per milliliter of urine demonstrated more than 90 percent reduction in gas phase ammonia from the control mixture. Specific results are shown in Table 2.

TABLE 2

| Yucca-70 Concentration (%) | Ammonia Measured (ppm) | % Inhibition of Released Ammonia |
| --- | --- | --- |
| 0 | 610 | — |
| 0.9 | 283 | 53.6 |
| 4.6 | 38 | 93.8 |
| 9.1 | 53 | 91.3 |

EXAMPLE 3

This Example is similar to Example 2 except that *Proteus mirabilis* was used instead of jack bean urease. Various concentrations of *Yucca schidigera* extract were studied to determine their efficacy for inhibiting this type of urease.

*Proteus mirabilis* (ATCC 29906) bacteria were recovered from frozen state by growing the appropriate bacterial coated MicroBank Bead (available from Pro Lab, Inc. of Austin, Tex.) in 10 ml of trypticase soy broth (TSB) (available from Difco of Ann Arbor, Mich.) in a 15 ml sterile loosely tightened screw capped conical tube overnight at 37 degrees Celsius. The tube was held stationary. Upon observation of turbidity, the bacterial suspension was checked for purity by isolation plate and Gram stain. Once determined that the isolate was *Proteus mirabilis,* a colony from the isolation plate was transferred to 10 ml of TSB in a 15 ml sterile screw capped conical tube and incubated overnight at 37 degrees Celsius under facultative conditions. Bacterial suspension from this overnight TSB culture was used.

An amount of a *Yucca schidigera* solution sold under the trade designation Yucca 70 by Sher-Mar Enterprises was thoroughly mixed in a vortex with 18 ml of urine and 2 ml of *Proteus mirabilis* prepared as described above. After a 22 hour incubation period at 37 degrees Celsius, the resulting mixture was analyzed with an ammonia detection tube and pH paper (available from Sigma Chemical Company of St. Louis, Mo.). A control mixture containing only 18 ml of urine, 2 ml of de-ionized water and 2 ml of *Proteus mirabilis* was also analyzed.

The results of the mixtures containing the yucca extract were compared to the control mixture. The final concentrations of the yucca extract analyzed were zero weight percent per volume (control mixture), 0.9 percent, 4.6 percent, and 9.1 percent. The 0.9 percent mixture containing 6.3 milligrams of yucca extract solids per milliliter of urine demonstrated substantially no reduction in gas phase ammonia from the control mixture and a pH about the same as the pH of the control mixture, i.e., 9.2. The 4.6 percent mixture containing 31.5 milligrams of yucca extract solids per milliliter of urine demonstrated about 60 percent reduction in gas phase ammonia from the control mixture and a pH of about 8.8, and the 9.1 percent mixture containing 63 milligrams of yucca extract solids per milliliter of urine demonstrated more than 90 percent reduction in gas phase ammonia from the control mixture and a pH of about 7.5. Specific results are shown in Table 3.

TABLE 3

| Yucca-70 Concentration (%) | Ammonia Measured (ppm) | % Inhibition of Released Ammonia |
|---|---|---|
| 0 | 710 | — |
| 0.9 | 850 | no effect |
| 4.6 | 285 | 59.9 |
| 9.1 | 52 | 92.7 |

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An absorbent article for absorbing body waste, said article comprising:
    a permeable liner having a body-facing surface oriented for facing a wearer when the absorbent article is worn and an absorbent-facing surface opposite the body-facing surface;
    an outer cover;
    an absorbent body positioned between the liner and the cover for absorbing body waste penetrating the liner; and
    a *Yucca* species extract positioned between the body-facing surface of the liner and the outer cover.

2. An absorbent article as set forth in claim 1 wherein the *Yucca* species extract is applied to the absorbent-facing surface of the liner.

3. An absorbent article as set forth in claim 2 wherein a composition comprising said *Yucca* species extract is applied to the absorbent-facing surface of the liner.

4. An absorbent article as set forth in claim 3 wherein the composition comprises at least about 0.001 percent *Yucca* species extract by weight.

5. An absorbent article as set forth in claim 4 wherein the composition comprises at least about 0.01 percent *Yucca* species extract by weight.

6. An absorbent article as set forth in claim 3 wherein the composition comprises less than about 1.0 percent *Yucca* species extract by weight.

7. An absorbent article as set forth in claim 2 wherein the *Yucca* species extract comprises *Yucca schidigera*.

8. An absorbent article as set forth in claim 7 wherein a composition comprising said *Yucca schidigera* is applied to the absorbent-facing surface of the liner.

9. An absorbent article as set forth in claim 8 wherein the composition comprises at least about 0.001 percent *Yucca schidigera* by weight.

10. An absorbent article as set forth in claim 9 wherein the composition comprises at least about 0.01 percent *Yucca schidigera* by weight.

11. An absorbent article as set forth in claim 8 wherein the composition comprises less than about 1.0 percent *Yucca schidigera* by weight.

12. An absorbent article as set forth in claim 1 wherein the *Yucca* species extract is held by the absorbent body.

13. An absorbent article as set forth in claim 12 wherein the absorbent body includes opposite outer faces and the *Yucca* species extract is held within the body between the outer faces.

14. An absorbent article as set forth in claim 12 wherein absorbent body includes opposite outer faces and the *Yucca* species extract is applied to at least one of said opposite outer faces of the absorbent body.

15. An absorbent article as set forth in claim 12 wherein a composition comprising said *Yucca* species extract is held by the absorbent body.

16. An absorbent article as set forth in claim 15 wherein the composition comprises at least about 0.001 percent *Yucca* species extract by weight.

17. An absorbent article as set forth in claim 16 wherein the composition comprises at least about 0.01 percent *Yucca* species extract by weight.

18. An absorbent article as set forth in claim 15 wherein the composition comprises less than about 1.0 percent *Yucca* species extract by weight.

19. An absorbent article as set forth in claim 12 wherein the *Yucca* species extract comprises *Yucca schidigera*.

20. An absorbent article as set forth in claim 19 wherein a composition comprising said *Yucca schidigera* is held by the absorbent body.

21. An absorbent article as set forth in claim 20 wherein the composition comprises at least about 0.001 percent *Yucca schidigera* by weight.

22. An absorbent article as set forth in claim 21 wherein the composition comprises at least about 0.01 percent *Yucca schidigera* by weight.

23. An absorbent article as set forth in claim 20 wherein the composition comprises less than about 1.0 percent *Yucca schidigera* by weight.

24. An absorbent article as set forth in claim 1 wherein a composition comprising said *Yucca* species extract is positioned between the body-facing surface of the liner and the outer cover.

25. An absorbent article as set forth in claim 24 wherein the composition comprises at least about 0.001 percent *Yucca* species extract by weight.

26. An absorbent article as set forth in claim 25 wherein the composition comprises at least about 0.01 percent *Yucca* species extract by weight.

27. An absorbent article as set forth in claim 24 wherein the composition comprises less than about 1.0 percent *Yucca* species extract by weight.

28. An absorbent article as set forth in claim 1 wherein the *Yucca* species extract comprises *Yucca schidigera*.

29. An absorbent article as set forth in claim 28 wherein a composition comprising said *Yucca schidigera* is positioned between the body-facing surface of the liner and the outer cover.

30. An absorbent article as set forth in claim 29 wherein the composition comprises at least about 0.001 percent *Yucca schidigera* by weight.

31. An absorbent article as set forth in claim 30 wherein the composition comprises at least about 0.01 percent *Yucca schidigera* by weight.

32. An absorbent article as set forth in claim 29 wherein the composition comprises less than about 1.0 percent *Yucca schidigera* by weight.

33. An absorbent article as set forth in claim 1 wherein the article is a diaper.

34. An absorbent article as set forth in claim 1 wherein the article is an infant care product.

35. A method of inhibiting production of ammonia from urine held adjacent a wearer's skin by an absorbent article, said absorbent article comprising a permeable liner having a body-facing surface oriented for facing a wearer when the absorbent article is worn and an absorbent-facing surface opposite the body-facing surface, an outer cover, and an absorbent body positioned between the liner and the cover for absorbing body waste penetrating the liner, said method comprising applying a composition including a *Yucca* species extract between the absorbent-facing surface of the liner and the outer cover.

36. A method as set forth in claim 35 wherein the composition applied between the absorbent-facing surface of the liner and the outer cover comprises at least about 0.001 percent *Yucca* species extract by weight.

37. A method as set forth in claim 36 wherein the composition applied between the absorbent-facing surface of the liner and the outer cover comprises at least about 0.01 percent *Yucca* species extract by weight.

38. A method as set forth in claim 35 wherein the composition applied between the absorbent-facing surface of the liner and the outer cover comprises less than about 1.0 percent *Yucca* species extract by weight.

39. A method as set forth in claim 35 wherein the *Yucca* species extract comprises *Yucca schidigera*.

40. A method as set forth in claim 39 wherein the composition applied between the absorbent-facing surface of the liner and the outer cover comprises at least about 0.001 percent *Yucca* species extract by weight.

41. A method as set forth in claim 40 wherein the composition applied between the absorbent-facing surface of the liner and the outer cover comprises at least about 0.01 percent *Yucca* species extract by weight.

42. A method as set forth in claim 39 wherein the composition applied between the absorbent-facing surface of the liner and the outer cover comprises less than about 1.0 percent *Yucca* species extract by weight.

* * * * *